United States Patent
Van Driessche et al.

(10) Patent No.: US 8,288,595 B2
(45) Date of Patent: *Oct. 16, 2012

(54) PLASTICISER ALCOHOL AND PRODUCTION IMPROVEMENT

(75) Inventors: Eddy Van Driessche, Eeklo (BE); Jean-Jacques G. Muls, Wemmel (BE); Arie Van Vliet, Sterrebeek (BE); Carl R. Beck, Baton Rouge, LA (US); Charles M. Yarbrough, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/401,257

(22) Filed: Feb. 21, 2012

(65) Prior Publication Data

US 2012/0149935 A1    Jun. 14, 2012

Related U.S. Application Data

(63) Continuation of application No. 12/767,343, filed on Apr. 26, 2010, now Pat. No. 8,143,459.

(60) Provisional application No. 61/183,575, filed on Jun. 3, 2009, provisional application No. 61/313,946, filed on Mar. 15, 2010.

(51) Int. Cl.
  *C07C 29/04* (2006.01)
  *C07C 67/08* (2006.01)

(52) U.S. Cl. .......................................... 568/899; 560/99
(58) Field of Classification Search .................. 568/899; 560/99

See application file for complete search history.

(56) References Cited

U.S. PATENT DOCUMENTS

| 5,306,848 A | 4/1994 | Vargas |
| 6,680,414 B2 | 1/2004 | Knoop et al. |
| 7,232,934 B2 | 6/2007 | Saleh et al. |
| 2005/0065384 A1 | 3/2005 | Saleh et al. |

FOREIGN PATENT DOCUMENTS

| EP | 1 219 584 | 7/2002 |
| GB | 2 142 010 | 1/1985 |
| WO | WO 2005/058782 | 6/2005 |

OTHER PUBLICATIONS

U.S. Appl. No. 61/183,575, filed Jun. 3, 2009, Van Driessche et al.

*Primary Examiner* — Sikarl Witherspoon
(74) *Attorney, Agent, or Firm* — Leandro Arechederra, III

(57) ABSTRACT

Embodiments of the invention disclosed herein relate to a process for the production of a $C_6$-$C_{15}$ alcohol mixture comprising the steps of: hydroformylating an olefin mixture comprising a branched $C_5$-$C_{14}$ olefin to form a hydroformylation product comprising aldehydes and formate esters, whereby the hydroformylation product has a net cold sap number from 15 to 38 mg KOH/g, and converting the aldehydes and formate esters to alcohols in a hydrogenation step comprising at least one first hydrogenation reactor comprising a fixed bed of a heterogeneous sulphided bimetallic catalyst.

21 Claims, No Drawings

PLASTICISER ALCOHOL AND PRODUCTION IMPROVEMENT

CROSS REFERENCE TO RELATED APPLICATION

This application is a continuation of Ser. No. 12/767,343, filed Apr. 26, 2010, now U.S. Pat. No. 8,143,459 now allowed, which claims the benefit of Ser. No. 61/183,575, filed Jun. 3, 2009, and Ser. No. 61/313,946, filed Mar. 15, 2010, the disclosures of which are incorporated herein by reference in their entireties.

FIELD OF THE INVENTION

The present invention relates to improvements in or relating to the production of an improved C6-C15 alcohol mixture, and to esters made from such alcohol mixtures. The alcohol mixtures provide improved esters of polycarboxylic acids, in particular phthalate esters, which are suitable as plasticisers for polymers.

BACKGROUND OF THE INVENTION

C6 to C15 alcohols are produced in large volumes throughout the world by the hydroformylation of olefins to produce aldehydes, followed by hydrogenation of the aldehydes to produce alcohols. The hydroformylation process is also referred to as the Oxo or oxonation process, and the alcohols may also be referred to as oxo-alcohols. The olefins that are used as feeds for the hydroformylation are generally oligomers of olefins that are obtained from petroleum feedstocks. Various processes may be used to produce the olefins used for hydroformylation. For example, the octenes that are used in the production of nonyl alcohol, which is produced in large volumes for the manufacture of plasticiser ester, may be produced by the dimerisation of butenes employing a nickel containing catalyst, e.g., by the Octol® or Dimersol® processes, or dimerisation on a zeolite or other acidic catalyst. These are processes which yield substantially pure octenes. Alternatively olefin mixtures averaging about eight carbon atoms may be obtained by the oligomerisation of olefin mixtures using acid catalysts such as phosphoric acid catalysts.

In both these processes, due to the petroleum origin of the olefins, the olefins typically contain impurities such as sulphur and chlorine which can have a damaging effect on the hydroformylation reaction and, in particular, the hydrogenation reactions. The hydrogenation reactions are performed by catalytic hydrogenation at elevated temperature and pressure and the conditions must be carefully controlled in order to optimise the yield and selectivity of the hydrogenation, ensure safe operation of the hydrogenation unit, secure commercially viable catalyst life and minimize side reactions.

Alternative processes for producing alcohols may comprise the hydroformylation of lower carbon number olefins, such as ethylene, propylene and butenes to the corresponding aldehyde or aldehyde mixtures containing one more carbon number than the starting olefin or olefins. These aldehydes, or mixtures thereof, are then subjected to aldolisation to produce condensation products, typically higher aldehydes containing an extra carbon-carbon double bond, often referred to as enals. These enals or enal mixtures may be hydrogenated to the corresponding saturated aldehydes or aldehyde mixtures, or directly to the corresponding alcohols or alcohol mixtures. Examples of products produced by such processes are 2-methylpentanol, 2-ethylhexanol, 2,4-dimethylheptanol and 2-propylheptanol, but other alcohols and alcohol mixtures produced in this way are also known.

Commercial C6-C15 alcohol mixtures may be produced from C5-C14 olefin mixtures by a process involving hydroformylation followed by hydrogenation. Hydroformylation typically uses a homogeneous metal catalyst, typically rhodium and/or cobalt, often in the carbonyl form. The removal of the metal catalyst may involve oxidizing the metal to a water soluble metal salt. The oxidation may use air as the oxidant.

The subsequent hydrogenation step typically uses a heterogeneous catalyst. Many hydrogenation catalysts are sensitive to poisoning, in particular by sulphur, and this often at relatively low levels. If the olefin feed mixtures contain traces of sulphur, it may be preferred to remove the sulphur before the hydroformylation step in order to protect a sulphur sensitive hydrogenation catalyst downstream. This step may be omitted if the selected hydrogenation catalyst is resistant to sulphur.

During the hydroformylation, the aldehydes that are formed by the main reaction may further react, with $H_2$ to form the alcohol that is often the prime product, with CO and $H_2$ to form a formate ester, and with two alcohol molecules present to form an acetal and water. Water is therefore typically added to the hydroformylation reaction, to promote hydrolysis of formate esters to form an alcohol and formic acid, and/or to push back the acetal formation reaction. In several of the known hydroformylation catalyst cycles, the formic acid byproduct from the hydroformylation step is a useful component. Part of the formic acid byproduct may also remain in the hydroformylation product.

The product from the hydroformylation step, typically after removal of the metal catalyst, may be routed directly to the subsequent hydrogenation step, or unreacted olefins may first be distilled away and optionally recycled, and the remainder of the stream may then be fed to hydrogenation, typically including formate esters, acetals and other heavies.

Also in the hydrogenation step, water is typically introduced, with the purpose to further promote the reduction of formate ester and/or acetals.

Formate esters may thus also during hydrogenation be hydrolysed and produce byproduct formic acid. Some hydrogenation catalysts are more resistant to the presence of formic acid as compared to others. Methanol may be formed as a byproduct from some of the reactions wherein formate esters are reacted away in the hydrogenation step. We have found that the formation of methanol during hydrogenation may depend on the type of hydrogenation catalyst, on the amount of water present, and on the hydrogenation conditions.

A reduction of the acetals in the hydrogenation step down to low levels is particularly important because any acetals left in the hydrogenation product end up as heavies in the bottom byproduct from the alcohol distillation step which typically follows downstream. Some hydrogenation catalysts are better in the removal of acetals as compared to others.

The selection of a hydrogenation catalyst may thus be directed by several criteria in addition to its activity in aldehyde hydrogenation. For example, a sulphided bimetallic catalyst in the hydrogenation step of the alcohol process has good activity in converting formate esters and reducing acetals to very low levels, while withstanding formic acid and sulphur impurities in the hydrogenation feed.

WO 2005/058782 discloses an alcohol process including the hydrogenation of a feed stream having a cold sap number of 38.5 mg KOH/g. The process uses staged water injection in order to improve the reduction of formate esters and of acetals during hydrogenation. WO 2005/058782 proposes to use sulphided bimetallic catalysts because they are not poisoned by sulphur, and proposes to reduce the acidity of the catalyst support in order to avoid excessive by-product formation. WO 2005/058782 is silent about any presence or formation of acids, methyl esters or heavy esters prior to or during the hydrogenation step.

U.S. Publication No. 2005/0065384 discloses an alcohol process including the hydrogenation of a commercially-obtained crude linear nonanal as the feed over supported bimetallic catalysts in their reduced and in their sulphided form. The hydrogenation feeds contain at most 4.5 wt % of formate esters of C9 alcohols, which corresponds to a net cold sap number of 14.68 mg KOH/g. U.S. Publication No. 2005/0065384 is silent about the formation of methanol and methyl esters during the hydrogenation step.

Where aldehydes are present, their corresponding carboxylic acids may be formed via various chemical pathways, such as by reaction with oxygen or by the reaction of two aldehydes with water to form an alcohol plus an acid. Carboxylic acid formation may therefore occur during the different steps of the alcohol process, such as during the hydroformylation, the hydroformylation catalyst removal, and the hydrogenation step. We have found that a sulphided bimetallic hydrogenation catalyst may lead to a higher carboxylic acid formation as compared to others.

These carboxylic acids are typically undesired in the alcohol production process. Their hydrogenation to alcohol is relatively difficult and slow. Having the same carbon number of the alcohol prime product, the acids are less volatile but remain relatively difficult to separate from the prime alcohol product. When distilled away, their downgrade into the heavy byproduct stream represent a loss of useful molecules. Because the separation by distillation is difficult, the acid containing heavy byproduct may also contain some alcohol, representing further loss of useful molecules.

We have also found that hydrogenation catalysts such as the sulphided bimetallic catalysts may enable esterification. The carboxylic acids may then react in the hydrogenation step with alcohol to form a heavy di-alkyl ester having twice the carbon number of the alcohol, and water. These heavy esters remain in the bottom of the alcohol distillation and represent an even more important loss of useful molecules as compared to the acid alone.

As methanol may be present during hydrogenation, the esterification of the carboxylic acid may also lead to the formation of methyl esters.

We have found that the methyl esters of the carboxylic acids having the same carbon number of the aldehydes, and thus also of the product alcohol, do not separate from the alcohol product mixture by distillation, and thus remain primarily as an impurity in the product alcohol mixture. We have also found that it is very difficult to analyse for such methyl esters in a C6-C15 alcohol mixture.

The methyl ester impurity in the alcohol product may cause problems when the alcohol product is further esterified to an ester derivative. A particular problem occurs when an ester derivative of a polycarboxylic acid or its anhydride is produced, such as a phthalate, an adipate, a trimellitate or a cyclohexane dioate ester. Several of these esters of polycarboxylic acids are used as plasticizers for a polymer, typically for polyvinyl chloride (PVC). We have found that during esterification, the methyl ester may be subject to transesterification, freeing up the methanol. The methanol moiety in the methyl ester may be replaced by a parent alcohol moiety and a di-alkyl ester is then formed which has two alkyl chains with typically the same carbon number as the parent alcohol that was used for the esterification. We have also found that when an ester of a polycarboxylic acid is produced, most of the aliphatic di-alkyl esters formed during esterification remain as an impurity in the product ester. This impurity is undesirable because it may increase the volatility of the ester product, and it may contribute negatively to its performance, such as to the reading in the fogging test, or to the light scattering film performance, of the plasticiser ester or of an article derived there from. This is particularly important for the automotive industry, but also for other applications such as when articles are produced for indoor use.

The methanol that is liberated by the transesterification of the methyl ester may end up in the water byproduct from the esterification process, where it represents an environmental burden in the disposal of the waste water. The methanol may also react with the acid or acid anhydride used in esterification, such as adipic acid or trimellitic or phthalic anhydride, to produce undesirable di-methyl phthalates or adipates, or equivalent di-esters with one methyl and one C6-C15 alkyl group, or a trimellitate with one or two methyl groups instead of the desired alkyl group with more carbon atoms.

The di-alkyl aliphatic esters that are produced can be carried with the desired ester during its purification and can remain as an impurity in the final ester product and large quantities can render the ester unsuitable for use as a plasticiser. Even in smaller quantities, they can impair the volatility of the plasticiser and affect the fogging performance of the plasticiser of the finished article produced therewith. The presence of these undesired esters can be detected and quantified by a GC analysis of the product ester. With phthalate esters for instance, these di-alkyl aliphatic (mono-)esters elute in the region that is called "Intermediates", i.e., the region of the phthalate ester GC spectrum where the "dimer" impurities elute. Also the methyl-containing tri- or di-esters will tend to elute typically before the peak of the main tri- or di-ester, because of their lower molecular weight.

There therefore remains the need for a process for producing an alcohol wherein the formation of carboxylic acids having the same carbon number as the alcohol is reduced, in particular during the hydrogenation step and with a sulphided bimetallic hydrogenation catalyst which is more active in acetal reduction, which has a better formic acid resistance or a higher resistance to sulphur poisoning. Preferably, also the esterification of such carboxylic acids is reduced. A further need remains for a process to produce an alcohol wherein the formation of the methyl esters of such carboxylic acids during the hydrogenation step is reduced, because of the product quality problems these methyl esters may create. There remains also a need for an alcohol that contains only a limited amount of such methyl esters. The downstream process producing an ester derivative from such an alcohol with a polycarboxylic acid, is in need for an alcohol that contains only low amounts of methyl ester, such that the environmental burden associated with disposal of its byproduct water is reduced, and also such that its ester product contains lower amounts of di-alkyl esters and/or di- or tri-esters having one or more methanol moieties, leading to a product of higher purity which provides improved performance during downstream processing and improved performance of the derived consumer product during its useful lifetime.

SUMMARY OF THE INVENTION

The applicants have found that the formation of carboxylic acids in the alcohol process, and also the methyl ester presence in the product alcohol, may be reduced by a combination of specific controls in the hydroformylation reaction together with other specific controls in the subsequent hydrogenation reaction step.

The invention therefore provides a process for the production of a C6-C15 alcohol mixture comprising the steps of:
  a. hydroformylating an olefin mixture comprising a branched C5-C14 olefin to form a hydroformylation product comprising aldehydes and formate esters, whereby the hydroformylation product has a net cold sap number from 15 to 38 mg KOH/g, and
  b. converting the aldehydes and formate esters to alcohols in a hydrogenation step comprising at least one first hydrogenation reactor comprising a fixed bed of a heterogeneous sulphided bimetallic catalyst, optionally followed by at least one second hydrogenation reactor connected downstream of the first reactor, wherein the feed to the hydrogenation step (b) is a liquid comprising at least a portion of the aldehydes and formate esters formed in step (a) and at least 2 wt % water, based on the liquid hydrogenation feed, and wherein the temperature in the first hydrogenation reactor is at most 200° C., preferably, from 150° C. to 200° C., more preferably in the range of from 160° C. to 180° C.

The process according to the invention produces the alcohol by first hydroformylating an olefin mixture to a product having a net cold sap number within a specified range, followed by a downstream hydrogenation step wherein the formation of carboxylic acids, and indirectly also of any heavy di-alkyl esters and/or methyl esters thereof, is controlled by a combination of a tight control of the water addition and of the reactor temperature.

The net cold saponification (in short also called net "cold sap") number is a measure for the presence of formate esters in the hydroformylation product. The presence of formate esters in the hydrogenation feed affects the amount of methanol that may be formed during the hydrogenation step. The controls in the hydrogenation step then lead to a controlled make of additional carboxylic acid, and thus to a lower presence of carboxylic acids in the hydrogenation step. With less acid, less of the di-alkyl esters are formed, and less associated yield loss is suffered. With less acid and less methanol, less methyl esters are formed in the hydrogenation step providing a product alcohol of increased purity. The water added further affects the esterification equilibrium, thereby further reducing the levels of heavy di-alkyl esters and of methyl esters in the hydrogenation product, bringing advantages in terms of alcohol product yield and quality.

In another embodiment, the invention provides a C6-C15 alcohol mixture containing at most 300 ppm by weight of methyl esters of C6-C15 carboxylic acids, preferably at most 250 ppm by weight, more preferably at most 200 ppm, yet more preferably at most 150 ppm, even more preferably at most 100 ppm and most preferably at most 50 ppm by weight.

This brings several advantages. For example, an esterification process using the alcohol according to the invention liberates less methanol from the transesterification of the methyl esters, such that less methanol ends up in its byproduct water, and the ester process thus enjoys a reduced environmental burden in the disposal of its waste byproduct water.

Also, the ester derivative of the alcohol of the invention with a polycarboxylic acid contains a limited amount of di-alkyl aliphatic mono-esters.

In yet another embodiment, the invention therefore provides a C6-C15 ester of a polycarboxylic acid containing C6-C15 di-alkyl aliphatic mono-esters in an amount less than the amount that may be generated by transesterification of the methyl esters in the alcohol mixture that is used in the esterification. The ester of the polycarboxylic acid preferably is a phthalate di-ester, an adipate di-ester, a trimellitate tri-ester, or a cyclohexanoate di-ester. The aliphatic di-alkyl esters have a number of carbon atoms in their acid moiety that is the same as the number of carbon atoms in the parent alcohol used in esterification, and the alcohol moiety has also that same number of carbon atoms.

The polycarboxylic acid for the ester according to the invention is preferably selected from phthalic acid, adipic acid, trimellitic acid, cyclohexane dicarboxylic acid, and the anhydrides thereof. When there are 200 ppm by weight of methyl esters present in the parent C6-C15 alcohol of the polycarboxylic acid ester production, the corresponding maximum possible amount of C6-C15 di-alkyl aliphatic mono-esters in the polycarboxylic acid ester can be calculated, and depends on the carbon number of the parent alcohol and on the nature of the polycarboxylic acid ester produced. The 200 ppm by weight of methyl esters may lead to at most the ppm by weight of di-alkyl aliphatic mono-esters in the polycarboxylic acid esters as shown in Table 1. The levels of di-alkyl aliphatic mono-esters corresponding to higher and lower levels of methyl esters can be calculated proportionally from the numbers in Table 1.

TABLE 1

| ppm by weight di-alkyl ester | Polycarboxylic acid ester | | | |
|---|---|---|---|---|
| Alcohol Carbon Number | Phthalate di-ester | Adipate di-ester | Cyclohexanoate di-ester | Trimellitate tri-ester |
| 6 | 187.9 | 199.9 | 184.6 | 203.8 |
| 7 | 202.9 | 214.8 | 199.6 | 218.7 |
| 8 | 216.0 | 227.7 | 212.8 | 231.5 |
| 9 | 227.5 | 239.0 | 224.3 | 242.6 |
| 10 | 237.7 | 248.9 | 234.5 | 252.4 |
| 11 | 246.8 | 257.6 | 243.7 | 261.1 |
| 12 | 254.9 | 265.4 | 251.9 | 268.8 |
| 13 | 262.2 | 272.4 | 259.2 | 275.7 |
| 14 | 268.8 | 278.8 | 265.9 | 281.9 |
| 15 | 274.8 | 284.5 | 272.0 | 287.5 |

The polycarboxylic acid ester according to the invention has a lower volatility and thus a higher permanence, and shows an improved performance in fogging or light scattering film tests. Flexible PVC articles produced with the ester according to the invention also enjoy the higher permanence of the plasticizer and the improved performance in fogging, light scattering film, or indoor volatility tests such as the FLEC or Nordtest.

The process according to the invention provides several further advantages.

Having less formate esters formed in hydroformylation consumes less synthesis gas in the hydroformylation step. Having less formate esters in the feed to hydrogenation also leads to a reduced formation of CO and/or $CO_2$ byproducts. CO may negatively affect the activity of some hydrogenation catalysts. The byproducts are gaseous components ending up in the offgasses from the hydrogenation process, making them less pure in hydrogen, and therefore less suitable for recycle to the hydrogenation process. The byproducts build up in the process when recycled, and the molecular weight of the hydrogenation offgas increases with more CO and/or $CO_2$, which increases the duty of the compressor required for any offgas recycle. Separating the useful $H_2$ from the undesired CO and/or $CO_2$ in the offgasses is typically not economical. With less CO and/or $CO_2$ to dispose of, typically also less useful $H_2$ has to be discarded together therewith.

DETAILED DESCRIPTION

Hydroformylation is a well-known process in which an olefin is reacted with carbon monoxide and hydrogen in the presence of a catalyst to form aldehydes and alcohols containing one carbon atom more than the feed olefin. This process has been operated commercially for many years and there have been two principle technology families used, one of which is known as the low or medium pressure oxo process family and which generally involves the use as catalyst of an organometallic complex of rhodium with organophosphorous ligands for providing the necessary stability at the lower pressures and operates at pressures from 10 to 100 Bar. The second process family is known as the high or medium-pressure process family and generally involves the use of an unmodified cobalt or rhodium based catalyst and typically operates at pressures from 100 to 350 Bar. Generally the low pressure processes are used for the hydroformylation of unbranched and terminal, primarily lower olefins such as ethylene, propylene and n-butenes, but also including n-hexene-1 and n-octene-1, or surfactant range Fischer-Tropsch olefin mixtures, whereas the high or medium pressure processes are primarily used for the hydroformylation of linear and/or branched higher olefins or mixtures such as those containing 5 or more carbon atoms. This process is widely used to produce what are known as "higher alcohols" or aldehydes or acids which are in the C6-C15 range particularly the C9-C13 range. The present invention is particularly applicable to the high pressure cobalt catalysed hydroformylation process since the production of formate esters is particularly high when that technology is employed.

The hydroformylation typically uses a homogeneously dissolved catalyst complex, which may be based on cobalt or rhodium, and sometimes palladium. Ligands may be used to modify the catalyst complex, usually being phosphorous based, and tributylphosphine is typically known to be used with cobalt metal. With rhodium, the ligands are typically organophosphines, with triphenylphosphine (TPP) or the oxide thereof being preferred, or organophosphites.

Where cobalt catalysed hydroformylation is used, the product is decobalted. In one embodiment, this is done by neutralising the active cobalt species $HCo(CO)_4$, with a base such as sodium hydroxide or carbonate in a decobalter. The decobalter conditions are such that the neutralization converts the hydrocobalt carbonyl to sodium cobalt carbonyl. Preferred conditions are to use a stoichiometric excess of sodium hydroxide or carbonate above the amount needed for cobalt neutralization, an excess of 100% to 200% particularly 140% to 180% is useful. The decobalter is typically operated at a temperature in the range 155° C.-165° C. and it is preferred that sufficient carbon dioxide and/or carbonate is present in the decobalter to ensure the formation of sodium cobalt carbonyl and to also buffer the pH in the range 7.8 to 8.5. This technique is described in more detail in WO 2006/122526.

Alternative embodiments use techniques for the decobalting of the product of cobalt catalysed hydroformylation by oxidative methods, and are described in WO 2008/128852, which are conveniently used together with the techniques of the present invention. Yet, other suitable techniques are described in U.S. Pat. Nos. 5,237,105, 5,218,134, and 4,625,067, and in copending patent application U.S. Ser. No. 61/092,835, and yet another suitable technique is described in copending patent application U.S. Ser. No. 61/092,833.

The preferred conditions for hydroformylation are described in WO 2005/058787 and these are preferably used in the present invention.

In order to improve the selectivity of the hydroformylation reaction, water may be present in the hydroformylation reactors. We have found that the injection of water reduces the formation of formate esters and heavy by-products. When used, water should be injected into the first reactor, and may also be injected into the second and subsequent reactors, if they are used, but we have found that this is not always essential. In a gas-lift reactor, the formation of a significant volume of a stagnant free water phase in the bottom can become an impediment or even an obstruction to the circulation of the reactor fluid. Gas-lift reactors from which any free water is continuously removed from the bottom have been described in WO 01/14297. If there is no water removal capability, the quantity of water that is introduced should preferably not exceed or not exceed by more than 10% or 20% the solubility of the water in the reaction mixture, to avoid the formation of a stagnant free water phase in the reactor. We have found that no more than 2 wt % of water based on the weight of olefin feed should be used in the first hydroformylation reactor and typically from 1.0 wt % to 1.75 wt % particularly 1.5 wt % should be used. The weight of the olefin feed being the weight of unsaturated materials in the feed which is typically above 95 wt % of the feed and frequently about 99 wt % of the feed. Where water is injected into the second reactor, similar considerations may apply depending on the design of the reactor. Due to the different liquid composition in the second reactor, the water solubility may be different in this reactor, and we prefer to use typically a total of 2.5 wt % water present based on the olefin feed. These amounts of water apply readily in the production of C6-C11 alcohols. They may have to be reduced for the production of heavier alcohols because of the lower water solubility of their hydroformylation reaction mixtures.

We have found that the injection of water provides a significant improvement in plant utilization as well as carbon monoxide utilization. The water should be injected in a manner that ensures good mixing of the water with the reactants and also prevents large fluctuations in the olefin to water feed ratios.

Accordingly, it is preferred that the water be injected into a fully operational reactor and when a loop reactor is used, it is preferred that the materials are circulating at a velocity of at least 0.6 meters/sec when the water is injected. It is also preferred that the water and the olefin are continuously introduced into the reactor at the desired water to olefin ratio.

In preparation for the hydrogenation phase the product from hydroformylation is preferably cooled, passed to a decobalting or demetalling and washing unit, filtered to further remove cobalt species and the use of pumice filters is particularly preferred for the removal of cobalt. At this stage the water content of the hydroformylation product is typically between 1 and 3 wt % water, which may be dissolved and/or in the form of entrained droplets. The presence of free water droplets by entrainment, such from the washing unit, may be further reduced by the use of a water coalescer. More details on a coalescer are disclosed in our copending application U.S. Ser. No. 61/092,833. The temperature of the product at this stage is typically between 40° C. and 80° C., more typically between 50° C. and 70° C., and especially 60° C. The product is then fed (with any further water addition if needed) to the first hydrogenation reactor. It may be preferred that the product passes in an upward direction through the first hydrogenation reactor since this flow mode results in improved heat transfer. Upward flow however increases the risk for water buildup in the reactor, in case a free water phase would exist. Downward flow may be preferred to avoid the risk for water layer buildup, and may also provide a better liquid and gas distribution under well defined hydraulic conditions, as explained in WO 2006/086067.

We have found that under the conditions in the first hydrogenation reaction in the process according to the invention, the aldehydes are hydrogenating fast to the corresponding alcohol, while the formation of acids is reduced. We believe that this beneficial effect is obtained by keeping the temperature in the first hydrogenation reactor limited to the specified maximum. This may be achieved by any of a series process features, such as a lower reactor inlet temperature or a partial recycle of the product of the first hydrogenation reactor, or of the hydrogenation product. Using partial recycle of a hydrogenation reactor product or the product of the hydrogenation section to the feed of the hydrogenation section has, in addition to its first benefit by dilution on lowering the reaction exotherm, a significant further advantage. While the aldehyde hydrogenation reaction rate is first order in aldehyde concentration, the acid formation via the Cannizzaro reaction involves two aldehyde molecules and is therefore second order in aldehyde concentration. The positive effect of the dilution on reducing the acid formation rate via the Cannizzaro reaction may thus be much stronger than the negative effect on the aldehyde hydrogenation rate. The intermediate or product recycle brings further the additional advantage that the water solubility of the total hydrogenation feed is increased, such that any entrained or injected water more readily dissolves into the organic stream, thereby reducing the risk of exposing equipment and/or catalyst to a free water phase, which may possibly build up inside the equipment, especially in a reactor operating in upflow mode, and which may cause corrosion of the equipment. A preferred hydrogenation section intermediate recycle operation is described in more detail in U.S. Pat. No. 4,877,358.

The preferred amount of water present during hydrogenation is a careful balance. On the one hand, a higher water presence may tend to increase the formation rate of acids from aldehydes, which is a disadvantage. On the other hand, a higher water presence favourably affects the equilibrium between acids and their esters, in this case both heavy di-alkyl esters and methyl esters. We have found that a minimum of 2 wt % of water in the feed to the first hydrogenation reactor is preferred, and that preferably a maximum of 3 wt %, based on the liquid hydrogenation feed, should not be exceeded. This balanced amount of water keeps the acid production under control, and also reduces the appearance of esters thereof in the product of the first hydrogenation reactor, and further downstream in the hydrogenation product. We prefer to include a second hydrogenation reactor downstream of and connected in series with the first hydrogenation reactor. Preferably this second hydrogenation reactor is loaded with a hydrogenation catalyst of the same type as in the first hydrogenation reactor. We prefer to operate such a second hydrogenation reactor at a higher temperature than the first hydrogenation reactor, preferably using a temperature of at least 180° C., more preferably in the range of from 190° C. to 210° C., typically at around 200° C. We have found that a higher temperature in the back end of the hydrogenation step brings the advantage of reducing the presence of acids, methyl esters and/or of heavier di-alkyl mono-esters in the product of the hydrogenation step. This reduces the loss of valuable molecules by esterification in the bottom of any of the downstream distillation towers, and the loss of these heavier ester molecules with the heavy byproduct from such distillation. It also reduces the methyl ester content in the alcohol product after distillation.

We prefer to use in the first hydrogenation reactor a pressure of at least 55 barg, preferably at least 60 barg. This provides sufficient partial pressure of hydrogen to drive the hydrogen consuming reactions. More preferably, we use a pressure of at least 120 barg, even more preferably at least 125 barg. At the higher pressure, we have found that the acid make is reduced, and thereby the loss of valuable molecules as di-alkyl esters in the heavy byproduct from distillation. A higher pressure, however, may lead to a higher methanol make from the formate esters in the hydrogenation feed, which may lead to a higher methyl ester content in the hydrogenation product, and thus in the product alcohol. We also prefer to use a pressure that is not more than 130 barg. Further pressure increases were found to have only negligible effects, while they further increase the investment cost of the equipment.

In a preferred liquid phase hydrogenation process, the product from the first hydrogenation reactor then passes in a line to the second hydrogenation reactor and it is preferred that the line be provided with an inlet for the injection of water and a mixer whereby the water and the product may be mixed to ensure that the water is dissolved and/or entrained in the product. It is preferred that from 1 wt % to 2 wt % of water based on the weight of the product be injected. The mixture then passes to the second hydrogenation reactor where it passes through the catalyst bed at a temperature of 180° C. to 210° C. in the presence of hydrogen. In the preferred embodiment the product flows downwardly in the second reactor.

Following the last hydrogenation reactor the product passes to a high pressure separator in which unreacted hydrogen may be flashed off and, if desired, recycled to the hydroformylation reactors as is described in WO 2005/058787. It is also possible to recycle some or all of this unreacted hydrogen to the hydrogenation reactors. In this embodiment only a portion of the unreacted hydrogen is passed to the hydroformylation reactors.

The product of hydrogenation following the separation of the hydrogen comprises a mixture of the desired alcohols, olefins and paraffins, alcohol dimers, acetals and traces of aldehydes and formates together with dissolved carbon dioxide and dissolved hydrogen and water, and aliphatic esters of carboxylic acids. The product may then be purified firstly through a coalescer to remove water, followed by fractional distillation to separate the C6-C15 alcohol from the lower boiling fraction of the mixture and a second distillation to separate the alcohol from the higher boiling fraction. Water and any methanol or other lower alcohols typically will be separated with the lower boiling fraction, and may settle out as a separate phase in the tower overhead system, from where they can be discarded or taken for further use. The presence of methanol can cause environmental problems requiring special disposal techniques and accordingly the reduction in the production of methanol according to the present invention is particularly beneficial.

Particularly with liquid phase hydrogenation, the hydrogenation reactors may be vertical tubes, provided with a jacket for temperature control and heat removal. They may be operated in upflow or in downflow mode. In the jacket, water or another suitable cooling medium such as an alkanol, preferably methanol, may be circulated using a pumparound system from which hot cooling medium may be withdrawn, and to which cold cooling medium may be supplied. Each reactor may be provided with a so-called conditioner, which is a heat exchanger one side of which is part of the cooling medium circulation, and which on the other side is for conditioning the reactor feed to the appropriate temperature before it passes to the reactor itself. Conditioning of the reactor feed is especially important when a reactor that is not a lead reactor contains relatively fresh and active catalyst, and therefore needs to be operated at start-of-run conditions, this typically requires a lower temperature. The upstream reactor on the other hand, may contain partially deactivated catalyst and therefore needs to be operating at mid-of-run or end-of-run conditions, which may require a higher temperature. Feed conditioning can therefore avoid a reactor feed that is too hot for an active catalyst to handle, and can therefore reduce the risk for temperature runaway.

In gas phase hydrogenation, the reactors may contain one of more fixed beds of catalyst, and cooler fresh or recycle hydrogen may be injected in the reactor, its feed or in between the catalyst beds in the reactor for temperature control.

The process according to the invention provides the additional benefit that it operates close to the economic optimum olefin conversion with respect to overall variable costs.

In hydroformylation the main reaction is the olefin reacting with CO and $H_2$ to form an aldehyde having one carbon atom more than the starting olefin. The hydroformylation reaction rate is first order with respect to olefin concentration. This was clearly demonstrated for pure olefins. When olefin mixtures are hydroformylated, especially those mixtures that are rich in branched olefins, not all olefins react at the same rate due to differences in the location of the olefinic bond and in branchiness. The apparent overall reaction rate on such mixtures may thus deviate significantly from first order. As a result, one percent extra olefin conversion is much more difficult to obtain at a higher olefin conversion level.

Minor amounts of olefins may react with $H_2$ to form paraffins. The paraffins formed have about the same boiling point as the starting olefins. In a boiling point GC of the hydroformylation product, these paraffins do not show separately from any unreacted olefins or from paraffins that were already present in the hydroformylation feed. It is therefore convenient, and standard practice, to express the olefin conversion for a hydroformylation process as "Conversion Ex Paraffin", i.e., excluding any paraffin make, thus without accounting for the olefins that may have converted to paraffins. This olefin conversion "Ex Paraffin" or "Ex Par." can readily be determined by boiling point GC analysis, and is a handy and useful tool in measuring the progress of the hydroformylation reaction. When the hydroformylation product is passed on without intermediate distillation to the subsequent hydrogenation step, the olefin conversion Ex Par may also be determined from a boiling point GC spectrum of the hydrogenation product. It is therefore a useful tool in monitoring the overall alcohol production process.

The aldehyde formed by the hydroformylation of an olefin may be the subject of consecutive reactions. The aldehyde may for instance hydrogenate to form an alcohol, and this reaction may be favourable when the alcohol is the desired product. Another consecutive reaction is where the aldehyde undergoes a second reaction with CO and $H_2$, converting the aldehyde to a formate ester:

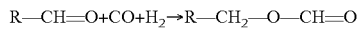

The aldehyde molecule in the formate ester is not necessarily lost from the alcohol production process. The formate esters may for instance be hydrolysed with water to form the desired product alcohol and formic acid:

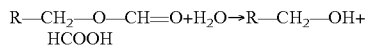

Minor amounts of water are typically added to the hydroformylation reaction and to the subsequent hydrogenation step for this purpose.

The formate esters are also recoverable as alcohols in the subsequent hydrogenation step, by a second pathway called hydrogenolysis, whereby methanol, CO, $H_2$ and/or $CO_2$ may be formed as byproducts, e.g., as follows:

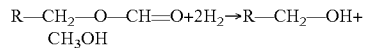

While the formation of formate esters during hydroformylation thus does not necessarily represent a loss of aldehydes for the production of desired alcohols, it does represent an additional consumption of CO and $H_2$ in the hydroformylation step, and the extra synthesis gas ends up as formic acid, methanol, CO, H2 and/or $CO_2$ further downstream. Only the $H_2$ byproduct may be considered useful, as it is liberated in the hydrogenation step where it supplements the $H_2$ gas added and participate in the hydrogenation reaction.

In the hydroformylation process, other consecutive reactions form heavies, such as ethers and ether-alcohols, many of which are not recoverable, or at least not as readily recoverable, as product alcohols and end up in the heavy oxonation fraction byproduct of the alcohol process. The heavy byproduct typically demands a lower economic return than the olefin feedstock or the light oxonation fraction byproduct containing the unreacted olefins. Their formation is thus typically undesirable in view of the process economics.

The various consecutive reactions involving aldehydes increase in rate as the aldehyde content of the reaction mixture increases. They become thus more important at higher conversions of the feed olefins. When olefin conversion is pushed up in a hydroformylation process, an operating point is reached where there is no more additional economic gain in converting more of the olefin feed, mainly because of the associated additional production of heavy byproduct. That operating point defines the economic optimum olefin conversion. The optimum olefin conversion depends on the type of olefin mixture. We have found however that, irrespective of the type of olefin feed, when the conversion of olefins is around its economic optimum for that feed type, the concentration of formate esters in the hydroformylation product typically is in the same range. We have found that the net cold sap of a hydroformylation product around the economic optimum of the overall process is in the range of from 15 to 38 mg KOH/g, more preferably in the range of from 16 to 35 mg KOH/g, even more preferably in the range of from 17 to 33 mg KOH/g, yet more preferably of from 18 to 30 mg KOH/g, and even more preferably in the range from 19 to 27 mg KOH/g, most preferably in the range of from 20 to 25 mg KOH/g.

Formate esters in a hydroformylation product can readily be measured by determining the cold saponification ("cold sap") number, using a well-known technique, such as based on ASTM D94 or DIN 51559. The raw cold sap number is a result of a potentiometric back titration. First, the free acids and the formate esters in the sample are saponified with an excess of KOH, preferably in ethanol as solvent. A selective hydrolysis of the formate esters is achieved by performing the saponification at room temperature. The back titration is typically performed with HCl, and the result is then conveniently converted to mg KOH/g. We have found that the raw cold sap number is not affected by the presence of methyl esters or heavier esters, as these do not appear to undergo hydrolysis at room temperature. A true measure of only the formate ester content is then obtained by deducting from the raw cold sap number the contribution of any free acids that were already present in the sample, to obtain the net cold sap number. The contribution of these acids to the raw cold sap number is readily determined by measuring the sample acidity, typically by a simple titration method, such as based on ISO standard 1843/2, and expressing the result in the same units, i.e., also in mg KOH/g.

A hot saponification number may also be determined by a method based on ASTM D94. In the hot sap method, all esters are hydrolysed by performing the saponification step with the excess KPH under ethanol solvent reflux conditions. The result from the titration is the raw hot sap number, which includes all free acids already present in the sample plus all acids obtained from hydrolysis of all esters, including the formate esters, the methyl esters, and the heavier esters. A net hot sap number is obtained by deducting the amount due to the free acids already present in the starting sample. In order to evaluate hydrogenation performance, we like to determine sample acidity, raw cold sap number and raw hot sap number. The raw cold sap number minus the acidity then gives the net cold sap number. The raw hot sap number minus the raw cold sap number gives a measure for the total presence of methyl esters plus heavier esters. Adding the acid number to this total then gives what we like to call "the total acid number", a useful measure of the total expected loss of useful molecules, assuming that the acids and heavy esters are distilled away from the alcohol during downstream distillation, and including also the methyl esters that remain in the product alcohol. We like to use this "total acid number" as guidance to evaluate and compare different hydrogenation performances.

The amount of water present in a liquid organic stream such as the hydroformylation product or the hydrogenation feed stream in the process according to the invention may be readily determined using a method known in the art. We prefer to use the Karl-Fischer titration method or equivalent for this purpose, because of its high accuracy.

The amount of methyl esters present in an alcohol mixture may be determined by Gas Chromatography combined with Mass Spectrometry (GCMS), preferably by the EI-GC-MS method. EI or EI+ stands for Electron Impact Ionization. We believe that the methyl ester molecules in the mass spectrometry undergo a McLafferty rearrangement, selectively forming as a major fragment a molecule fragment that is rather specific for the methyl ester and which has a molecular weight of 74. Without being bound by theory, we believe the fragment formed is $CH_3$—O—COH=$CH_2$. This fragment is believed to be formed independent of the structure and carbon number of the alkyl chain of the acid moiety of the methyl ester. We prefer to use a polar column for the GC, such as the FFAP type column from a supplier such as Hewlett Packard, in which methyl esters tend to elute ahead of alcohols having the same alkyl chain, and we prefer to integrate all the peaks giving the 74 molecular weight fragment in the GC region where alcohol molecules or their precursors elute. The total presence of methyl esters in an alcohol mixture sample may be readily obtained by this integration. The accuracy of the method depends on a good separation of peaks in the GC, and we prefer to use a GC column of 50 m×0.32 mm ID×0.5 µm, an oven temperature starting at 60° C. and increasing to 130° C. at a rate of 5° C. per minute, and further increasing to 240° C. at a rate of 25° C. per minute. We prefer to use an injector temperature of 250° C., a constant flow volume of 1.5 ml/min of Helium as the carrier gas, a split ratio of 1/150 and an injection volume of 1.0 µl. For the Mass Spectrometry, we prefer to use interface temperature of 240° C. and a full scan acquisition with 5.0 scans per second. We prefer the full scan above a Single Ion Monitoring (SIM) approach, because it allows to verify whether the peak giving the 74 molecular weight fragment is most likely a methyl ester. This allows weeding out any alcohol peaks that may also have given a 74 molecular weight fragment as a minor fragment. For a C9 alcohol mixture, we prefer to use a scan range (expressed in atomic mass units (a.m.u.)) of 35-200 and to start the acquisition at 4.5 minutes and stop it at 15.5 minutes.

We have found that for relatively complex mixtures of isononyl alcohols, a detection limit of 200 ppm by weight in total is readily achievable. By improved parameter tuning this detection limit may be further reduced to 50 ppm by weight or below. For more simple mixtures of isononyl alcohols, such as the isononyl alcohols derived from octenes obtained via the Octol® or Dimersol®-X process, the detection limit may be lower, down to the level of about 10 or 20 ppm by weight. For a further improved accuracy and lower detection limit, a two dimensional MS-MS technique may be applied.

We have found that these EI-GC-MS methods to determine methyl ester content in alcohol mixtures are fast and have a low detection limit compared to alternatives. The drawback is that there may be methyl esters present having a branch on the second carbon of their acid moiety, in which case the corresponding fragment produced in the Mass Spectrometry has a molecular weight that is different from, i.e., higher than 74. These methyl esters are then not detected with the above method, but we have found that their presence is usually small and may for practical purposes be neglected in most circumstances, except when the aldehydes to be hydrogenated are produced by aldolisation, in which case practically all of the molecules have a branch in their alkyl chain on the second carbon from the oxygen atom.

We have found that the presence of methyl esters may also be determined by $^{13}$C-NMR. This NMR method is not affected by any branching on the second carbon, and may thus be more selective and more appropriate for alcohols made by a process including aldolisation. Because of the lower sensitivity, a quantitative $^{13}$C-NMR method may require a long accumulation time, such as at least 10 hours.

We have found that on a scale of 0 to 220 ppm relative to tetramethyl silane (TMS), and using deutero acetone instead of the more typical deutero chloroform ($CDCL_3$) as solvent, the methoxy group of the methyl ester can be detected between 51.2 and 51.4 ppm, and that this is separate from the resonances of the methoxy group of methanol and methyl ethers. Because other peaks, such as a $CH_2$ group between two branches, can also be present in the 50 to 52 ppm region, we prefer to complement this measurement with another experiment, named Distortionless Enhancement by Polarization Transfer (DEPT). This additional experiment leads to 4 different spectra, showing specifically methyl, methylene, methine and all the protonated carbons, and from which it is possible to detect selectively the $CH_3$ peak from the methoxy group, even in a crowded region of the spectrum. All other methyl groups arising from the alkyl chains are detected between 31 and 5 ppm and do not interfere. Quantification can be done relative to the integration of the ethoxy function of the alcohols, appearing between 60 and 72 ppm, and by taking into account the molecular weight of the alcohol and of the methyl ester. A detection limit of 200 ppm by weight was readily obtained, and a longer acquisition time may further increase the sensitivity of the measurement.

We prefer to include into the process according to the invention an additional step, preceding the hydrogenation step (b), for reducing the level of formate esters in the liquid feed to the hydrogenation step (b). Having less formate esters in the hydrogenation feed will reduce the formation of methanol during hydrogenation, and therefore lead to a lower presence of methyl esters in the hydrogenation product, and thus also in the product alcohol mixture.

We prefer to reduce the format esters in the feed to hydrogenation by hydrolysis. This may for instance be achieved by contacting the product of the hydroformylation step (a), or the feed to the hydrogenation step (b), in the presence of water and preferably also of hydrogen, with alumina ($Al_2O_3$). On the alumina, the formate esters will at least partly hydrolyze to the alcohol plus formic acid, and the formic acid may decompose to CO plus water. Suitable conditions for the hydrolysis step are described in U.S. Pat. No. 3,935,285 for the hydrolysis of formate esters, and in U.S. Pat. No. 5,059,718 and U.S. Pat. No. 4,401,834 as described for the hydrolysis of acetals. U.S. Pat. No. 3,935,285 describes the distillation of a decobalted C9 hydroformylation product obtained from diisobutylene, and treating the distillation bottom product containing 15% of formic acid esters of the C9 alcohols with water at 300° C. over alumina to obtain hydrolysis, and hydrogenating the treated product using a nickel catalyst. The presence of 15% formic acid esters of C9 alcohol corresponds to a net cold sap number of 48.9 mg KOH/g. In U.S. Pat. No. 4,401,834 the presence and variation of acids and total esters in the process streams is monitored by giving acid number and the ester number as determined by the hot saponification method.

We have also found that cuprous chrome catalyst, such as described in WO 2005/058782 and exemplified by G 22 RS available from Süd-Chemie and Cu 1155 T available from Engelhard, now BASF catalysts LLC, is a particularly suitable catalyst to hydrolyse formate esters, even in its spent or poisoned form when its activity for aldehyde hydrogenation has already significantly been reduced. The advantage of using a cuprous chrome catalyst for formate ester hydrolysis is that the breakdown of the formate ester generates additional hydrogen, together with $CO_2$. The liberated hydrogen then becomes readily available for hydrogenation of an aldehyde, so that less hydrogen is needed in the hydrogenation step and it may be operated with a lower stoichiometric excess, but also a part of the aldehydes in the hydrogenation feed stream may already be hydrogenated in the formate ester hydrolysis step, thereby reducing the exotherm in the first hydrogenation reaction. All these factors are leading to a lower acid make on the sulphided bimetallic catalyst in the hydrogenation reactors, primarily in the first one. Additional hydrogen may be added in a hydrolysis step that uses a catalyst that also catalyses the hydrogenation reaction, such as the cuprous chrome catalyst. We prefer to operate the cuprous chrome hydrolysis step at a pressure of from 50 to 60 barg, preferably 55 barg, because at higher pressures the hydrolysis step may produce more methanol byproduct.

In one embodiment of the invention, the level of formate esters is reduced by contacting the liquid feed to the hydrogenation step (b) with a cuprous chrome catalyst in the presence of hydrogen and at least 2 wt % of water, based on the total liquid feed.

Sulphided bimetallic hydrogenation catalysts suitable for the process according to the invention are disclosed in WO 2005/058782, U.S. Publication No. 2005/0065384, U.S. Pat. No. 5,306,848, U.S. Pat. No. 6,278,030, or U.S. Pat. No. 5,382,715. We prefer to select a catalyst from the group consisting of sulphided Co oxide/Mo oxide, sulphided Ni/W—O, and sulphided Ni oxide/Mo oxide. Such catalysts are typically produced in their metal oxide form but are then sulphided with a sulphur precursor such as alkyl sulphides but preferably $H_2S$, to form the activated catalyst in its sulphide form. Also particularly suitable are the reduced nickel-molybdenum catalysts, e.g. carried on alumina support, that are disclosed in X. Wang et al, "Characterization of Active Sites over Reduced Ni—Mo/$Al_2O_3$ Catalysts for Hydrogenation of Linear Aldehydes", J. Phys. Chem. B 2005, 109, pp. 1882-1890, which catalysts we have found are also suitable for hydrogenation for branched aldehydes. These catalysts preferably contain no, or only small amounts of phosphorus, such as 0-1.0 wt % P, more preferably 0-0.5 wt % P, as disclosed in U.S. Pat. No. 5,382,715. Most preferably they are substantially free of phosphorus, as disclosed in U.S. Pat. No. 5,399,793.

We prefer to convert as much as possible of the aldehydes in the first hydrogenation reactor under the specified conditions, in order to suppress acid formation and thereby the formation of methyl esters and heavy esters. Over time the hydrogenation activity of the catalyst in the first hydrogenation reactor will decrease to below its initial activity. The temperature in the first hydrogenation reactor may then be increased to compensate for that loss of activity, but we prefer to stay within the limits specified. The loss of catalytic activity in the first hydrogenation reactor may then lead to an increase of methyl esters present in the product alcohol. When the level of methyl esters in the product alcohol becomes unacceptable, we prefer to introduce a third hydrogenation reactor into the process, comprising a heterogeneous sulphided bimetallic catalyst having a higher hydrogenation activity than the catalyst in the first hydrogenation reactor, and we prefer to introduce this third hydrogenation reactor into service as part of the process connected to and in series upstream of the first hydrogenation reactor. The first hydrogenation reactor then becomes situated in second or in tail end position, and its hydrogenation conditions may be adjusted accordingly and similar to those in the second hydrogenation reactor.

Also the catalyst activity in the second hydrogenation reactor may reduce over time. Subsequent to the introduction of the third hydrogenation reactor, the first or the second hydrogenation reactor may be removed from service as part of the process. This decommissioning may be followed by a regeneration of the catalyst in the hydrogenation reactor removed from service, or by a replacement of its catalyst with a regenerated or a fresh catalyst of the same type.

The alcohol mixture according to the invention may contain alcohol molecules having different carbon numbers. The carbon numbers of the alcohols in an alcohol mixture may be determined using the methods described in WO 2006/012989. From such an analysis, an average carbon number, typically averaged on a weight basis, for the alcohol mixture may be determined. We prefer to produce an alcohol having an average carbon number in the range of from 8 to 10.5, preferably from 8.5 to 9.5. We prefer the mixture to contain at least 90 wt % of alcohols having from 8 to 11 carbon atoms, most preferably from 9 to 10 carbon atoms.

The alcohols produced by the present invention may be used in the production of esters. The esters are prepared by esterification of acids and/or their anhydrides with the alcohols of the invention.

The esterification process comprises the following steps: a) adding the acid and/or anhydride and an excess of the alcohols to a reaction vessel; and b) heating the reaction mixture to a temperature at about or above the boiling point of the alcohol and maintaining a pressure sufficient to obtain boiling of the reaction mixture. The acid and/or anhydride and the alcohols are thereby converted to an ester. Water and some of the unreacted alcohol are removed from the reaction vessel and the alcohol removed may be recycled to the vessel.

The esterification process is preferably conducted in the presence of a catalyst. Typical esterification catalysts of commercial importance are sulfuric acid, methane sulfonic acid (MSA), para-toluene sulfonic acid (pTSA), stannous alcoholates or oxides, and titanium alcoholates. U.S. Pat. No. 3,056,818 discloses titanium esterification catalysts and is incorporated herein by reference, the more commonly used catalysts being tetra-isopropyl titanate and/or tetra-octyl titanate including tetra iso-octyl titanate More details on how the esterification process may be conducted, may be found in U.S. Pat. Nos. 5,324,853, 5,880,310 and 6,355,817, and particularly in WO 2005/021482, WO 2006/125670, WO 2008/110305 and WO 2008/110306, which are incorporated herein by reference.

The esterification process may further include one or more of the following steps: removing excess alcohol by nitrogen or steam stripping; adding adsorbents such as alumina, silica gel, activated carbon, clay and/or filter aid to the reaction mixture following esterification before further treatment; adding water and base to simultaneously neutralise the residual organic acids and to hydrolyse the catalyst (if present); filtering off solids from the ester mixture containing the bulk of the excess alcohol; removing water by flashing or steam or nitrogen stripping under vacuum and recycling of the alcohol or acid into the reaction vessel; and removing solids from the stripped ester in a final filtration.

In another embodiment, the invention provides for a process further comprising the esterification of the alcohol product or product mixture with an acid or anhydride to form an ester. The acid or anhydride is preferably selected from the group consisting of benzoic acid, phthalic acid, adipic acid, trimellitic acid, cyclohexanoic acid, cyclohexanoic dibasic acid, pyromellitic acid and their anhydrides. Particularly the phthalate esters, typically produced from phthalic anhydride, are of significant commercial importance.

The ester molecules produced using the process of the invention may comprise aromatic rings, such as alkyl benzoates, di-alkyl phthalates or tri-alkyl trimellitates. The aromatic rings in these ester molecules may be hydrogenated to produce the corresponding cyclohexanoic equivalents, such as mono-alkyl, di-alkyl or tri-alkyl cyclohexanoates. In particular, DINP may be further hydrogenated to form di-isononyl cyclohexanoate. The process of the invention may therefore be for the production of a phthalate di-ester, in particular DINP, and further comprise the hydrogenation of the phthalate di-ester to the corresponding cyclohexanoate, in particular di-isononyl cyclohexanoate. Suitable hydrogenation processes to produce such cyclohexanoates are disclosed in EP 1042273, U.S. Publication Nos. 2004/0260113, 2006/0149097, 2006/0166809, or WO 2004/046078.

In yet another embodiment, the invention therefore provides a process wherein the ester is a phthalate and further comprising the hydrogenation of the phthalate ester to a hexahydrophthalate ester.

Since their introduction in the middle of the 20th century, esters of C6-C15 alcohols have gained widespread use as plasticisers for PVC. PVC compounds prepared with phthalate esters of C6-C15 alcohols are used in many different market segments; these include electrical wire insulation, flexible vinyl flooring, vinyl coated wallpaper, vinyl shower curtains, synthetic leather, vinyl and boat covers, vinyl swimming pool liners, vinyl stationary products such as notebook covers, and tarpaulins.

Esters of C9 rich alcohols are often preferred because the C9 esters offer the best balance of properties when used as plasticisers, such as with PVC. A variety of other mono, di and tri esters are also known and used as plasticisers for plastics such as PVC.

One of the most important performance characteristics for a plasticiser, when used in PVC compound is its permanence, i.e., its resistance to water extraction, migration and in particular loss by volatility.

In particular, with phthalate esters but also with trimellitates and adipates, the di-alkyl aliphatic (mono-)ester originating from the methyl esters contaminating the alcohol contributes to volatility loss during processing and use, and especially in fogging performance.

The low content of these di-alkyl aliphatic (mono-)esters therefore brings improved fogging performance for PVC articles made with the plasticiser esters of the present invention.

Although the C9-rich esters offer advantages over the pure C8 esters with lower emissions, the level of emission is often not acceptable for some end-users. For products used in the interior passenger compartment for automobiles, manufacturers often develop specifications on the maximum level of emissions which can be released as the automobile sits in the sun. These emissions can result in the development of a "fog" or "light-scattering-film" that condenses or forms on the inner side of the windscreen. Currently, no pure C8 phthalate esters and no branched C9 phthalate can satisfy the specifications which require a maximal fog formation observed after 3 hours at 100° C. in a fog testing apparatus. To meet these performance criteria, phthalate esters of branched or linear C10 and C11 alcohols or phthalate esters based on the more expensive linear C9 alcohols (such as Jayflex® L9P) or esters of trimellitic anhydride are used.

There is therefore a continuing need for alcohols which will enable the production of plasticisers with an improved balance of properties, in particular an improved combination of low volatility and low viscosity, and the quality to pass the fog test. Accordingly, the phthalate, cyclohexane dioate, trimellitate and adipate esters of the present invention have low fogging properties which are highly desirable for use in automotive interior applications.

Phthalate esters prepared from the alcohol mixture according to the present invention provide a PVC plasticiser which has all the performance advantages associated with conventional phthalate esters, while PVC formulations containing the plasticisers dry-blend faster, i.e., the C8-C10 phthalate mixtures process faster than corresponding formulations containing dioctyl phthalate. When compared to the use of other known branched phthalate esters as plasticisers for PVC, the phthalate esters according to the present invention provide an improved combination of properties including improved processing efficiency, better low temperature performance, lower emission release during processing, as well as lower emission release during the use of the shaped article made from the plasticised PVC (such as fogging). Thanks to the lower volatility, these phthalate esters also provide a lower contribution to the buildup of Semi-Volatile Organic Compounds (SVOCs) in indoor air. SVOCs are currently defined as compounds boiling in the range delimited by normal hexadecane (n-C16) and up to C40.

Benzoate esters of the particular C8-10 alcohol mixture according to the present invention provide a lower contribution to the buildup of Volatile Organic Compounds (VOCs) in indoor air, as measured by the FLEC and Chamber Emission Test, as measured by ENV norm 13419, the VOC test being ENV 13419-3 and the FLEC and Chamber Emission test being ENV 13419-2. The benzoate esters also bring beneficial effects on the low temperature performance of the final flexible PVC article.

The acid or anhydride employed in the production of the esters from the alcohols of the invention is preferably organic. Examples of the organic acid or its anhydride that may be used in the esterification reaction include aromatic monocarboxylic acids typified by benzoic acid, and folic acid; polybasic aromatic carboxylic acids or anhydrides thereof, such as phthalic acid, phthalic anhydride, isophthalic acid, terephthalic acid, trimesic acid, trimellitic acid, trimellitic anhydride, pyromellitic acid, pyromellitic anhydride, benzophenonetetracarboxylic acid and benzo-phenonetetracarboxylic anhydride; polybasic aliphatic carboxylic acids such as adipic acid, sebacic acid and azelaic acid and citric acid; polybasic unsaturated aliphatic carboxylic acids such as maleic acid and fumaric acid; and aliphatic monocarboxylic acids such as oleic acid and stearic acid. The various phthalic acids or anhydrides are preferred. The alcohols employed in the esterification may be used singly or in combination as required. C7-C13 alcohols are preferably employed to make plasticiser esters and C9-C11 alcohols, especially the C10 and C11 alcohols are preferred especially in the production of plasticiser esters.

In one embodiment of the process, the esterification reaction is conducted by adding an alcohol to an organic acid or its anhydride, and reacting the mixture, preferably at from 150° C. to 220° C. and preferably for from 1 to 4 hours, in the presence of an organic metal compound catalyst in an inert gas atmosphere while removing water formed. The reaction time is preferably at the lower end of the range, e.g., from 1.5 to 2 hours, and optimally even less than 1.5 hours. A base and water, preferably in the form of an aqueous base, is added to the resulting reaction solution to neutralise any unreacted acid and/or mono-ester and to hydrolyse the catalyst. It is also preferred to remove any free water after the crude ester has been treated with the base and before filtration, particularly if the treatment has been with aqueous base. Preferred bases include alkali metal salts, particularly sodium salts, like sodium carbonate, and alkali metal hydroxides, like sodium hydroxide, e.g., aqueous sodium hydroxide. Any excess alcohol is recovered typically by stripping (which advantageously removes alcohol, water and other light materials) and the resulting ester product is then purified to obtain a plasticiser.

The contaminants in the plasticiser ester may belong to the family of acidic residues, unreacted alcohol, catalyst residues, water and the contaminants that were already present in the alcohol feed, most of these being so-called monomeric components that are eluted in the so-called "light ends" region of the plasticiser Gas Chromatogram or GC-spectrum, as discussed later. The crude esters may also contain byproducts, such as alcohol (di-alkyl)ethers, benzoate esters, monoesters from dibasic acids, alcohol oxo acid esters, hemiacetals and vinyl ethers (these are so-called dimeric components and are often collectively called "ethers" or "intermediates" due to their elution in the plasticiser Gas Chromatogram or GC-spectrum between the monomeric light ends and the "trimeric" diesters). Many of these dimeric materials, as well as acetals which are "trimeric" compounds, may become hydrolysed during later stages in the process to form odour formers such as aldehydes and/or other light ends. Methods for the treatment of the esters are described in WO 2005/021482 and WO 2006/125670.

The invention is illustrated by means of the following examples.

EXAMPLES

A C9 hydroformylation product was produced by hydroformylating a mixture of octenes which was produced by oligomerization of n-butenes over H-ZSM-57 catalyst. The hydroformylation product contained, by weight and as analysed by GC, about 12.3% olefins plus paraffins, 62.7% of the total of aldehydes, alcohols and formate esters, 17.9% of acetals and 7.1% of other heavies. The hydroformylation product was further characterised by a carbonyl number was 200 mg KOH/g, an acid number of 3.22 mg KOH/g, a raw cold sap number of 35.61 mg KOH/g. The net cold sap number was thus 32.39 mg KOH/g.

This C9 hydroformylation product was fed at a rate of 440 ml/h, together with a recycle of 800 ml/h of hydro product recycle, to a first hydrogenation reactor containing 250 ml of sulphided Ni/Mo catalyst, operating at a pressure of 80 barg and a temperature of 180° C., with an excess hydrogen of 400% and with 2.9 wt % of water in the hydrogenation feed. The product of the first hydrogenation reactor contained, by weight and as analysed by GC 0.1% of methanol, 12.4% olefins plus paraffins, 80.8% of the sum of aldehydes, alcohols and formate esters, 1.1% of acetals and 5.7% of other heavies. The product of the hydrogenation reactor was further characterised by a carbonyl number of 6.9 mg KOH/g, an acid number of 5.52 mg KOH/g, a raw cold sap number of 10.61 mg KOH/g and a raw hot sap number of 12.15 mg KOH/g. The net cold sap number was thus 10.61−5.52=5.09 mg KOH/g. The total presence of heavy di-alkyl esters plus methyl esters was thus equivalent to 12.15−10.61=1.54 mg KOH/g, and the total loss of valuable molecules equivalent to 1.54+5.52=7.06 mg KOH/g. The product of the first hydrogenation reactor contained 161 ppm by weight of methyl esters, mostly methyl nonanoate.

In another experiment the influence of the second hydrogenation step, on residual methyl esters and on yield loss was evaluated. An experiment performed over the same catalyst, at 190° C., 120 barg, with a flow of 407 ml/h and without any recycle or further water addition. The experiment demonstrated that the methyl ester content in the product obtained from the first hydrogenation reactor can be reduced in the second hydrogenation reactor by 40%, and that the loss of valuable molecules, expressed as "min acid make" was reduced by 50%. In addition, the final aldehyde concentration (as measured by carbonyl number) and formate esters (from the net cold sap number) had essentially disappeared. The hydrogenation product of the above experiment, when it would include a second hydrogenation reactor, therefore would contain 97 ppm by weight of methyl esters. This hydrogenation product is typically foreseen to be distilled, to separate away on one hand olefins plus paraffins as the light oxonation byproduct fraction (LOF), and on the other hand the heavies as heavy oxonation byproduct fraction (HOF) containing most of the acids and the di-alkyl esters. The distillation would result in the methyl esters being concentrated up into the product alcohol to a level of 97/0.808=120 ppm by weight.

Based on other experiments operating the first hydrogenation reactor on the same feed, the same flow rates and at the same temperature, but at a pressure of 120 barg, it is known that the acid number may be reduced to below 3.00 mg KOH/g, and the total loss of valuable molecules may as a result be reduced to an equivalent of 9.13 mg KOH/g, i.e., less than 75% of the loss obtained when the first hydrogenation reactor was operating at 80 barg. At the higher pressure, the methyl ester in the first hydrogenation reactor product would move up to around 225 ppm by weight. After having passed the hydrogenation back end section, the hydrogenation section product would contain about 145 ppm by weight of methyl esters. The product alcohol distilled from this hydrogenation section product would contain about 180 ppm by weight of methyl esters.

Having now fully described this invention, it will be appreciated by those skilled in the art that the invention can be performed within a wide range of parameters within what is claimed, without departing from the spirit and scope of the invention.

What is claimed is:

1. A process for the production of a $C_6$-$C_{15}$ alcohol mixture comprising the steps of:
   a. hydroformylating an olefin mixture comprising a branched $C_5$-$C_{14}$ olefin to form a hydroformylation product comprising aldehydes and formate esters, whereby the hydroformylation product has a net cold sap number from 15 to 38 mg KOH/g, and
   b. converting the aldehydes and formate esters to alcohols in a hydrogenation step comprising at least one first hydrogenation reactor comprising a fixed bed of a heterogeneous sulphided bimetallic catalyst, optionally, followed by at least one second hydrogenation reactor connected downstream of the first hydrogenation reactor;
   wherein the feed to the hydrogenation step (b) is a liquid comprising at least a portion of the aldehydes and formate esters formed in step (a) and at least 2% water by weight, based on the liquid hydrogenation feed, and
   wherein the temperature in the first hydrogenation reactor is at most 200° C.

2. The process of claim 1, wherein the temperature in the first hydrogenation reactor is from 150 to 200° C.

3. The process of claim 1, wherein the temperature in the first hydrogenation reactor is from 160 to 180° C.

4. The process of claim 1, wherein the process further comprises a second hydrogenation reactor in step (b) and the temperature in the second hydrogenation reactor is at least 180° C.

5. The process of claim 4, wherein the temperature in the second hydrogenation reactor is from 190 to 210° C.

6. The process of claim 1, wherein the amount of water in the liquid feed to step (b) is from 2 to 3% by weight.

7. The process of claim 1, wherein the pressure in the first hydrogenation reactor is at least 55 barg.

8. The process of claim 1, wherein the pressure in the first hydrogenation reactor is at least 60 barg.

9. The process of claim 1, wherein the pressure in the first hydrogenation reactor is at least 120 barg.

10. The process of claim 1, wherein the pressure in the first hydrogenation reactor is at least 125 barg.

11. The process of claim 1, wherein the pressure in the first hydrogenation reactor is from 55 to 130 barg.

12. The process of claim 1, wherein the heterogeneous sulphided bimetallic catalyst is selected from the group consisting of sulphided Co oxide/Mo oxide, sulphided Ni/W, sulphided Ni oxide/Mo oxide, and mixtures thereof.

13. The process of claim 1, wherein the hydrogenation step (b) is preceded by a step to reduce the level of formate esters in the liquid feed to hydrogenation step (b).

14. The process of claim 13, wherein the level of formate esters is reduced by hydrolysis.

15. The process of claim 13, wherein the level of formate esters is reduced by contacting the liquid feed with a cuprous chrome catalyst in the presence of hydrogen and at least 2% by weight of water, based on the total liquid feed to the hydrogenation step (b).

16. The process of claim 1, wherein the process further comprises a second hydrogenation reactor in step (b) and when the activity of the catalyst in the first hydrogenation reactor has decreased to below its initial activity, a third hydrogenation reactor comprising a heterogeneous sulphided bimetallic catalyst having a higher activity than the catalyst in the first hydrogenation reactor is introduced into service located upstream of the first hydrogenation reactor.

17. The process of claim 16, wherein, subsequently to the introduction of the third hydrogenation reactor, the first or the second hydrogenation reactor is removed from service, optionally, followed by regenerating the catalyst in the reactor removed from service or replacing the catalyst in the reactor removed from service with a regenerated and/or a fresh catalyst.

18. The process of claim 1, wherein the process further comprises esterifying the $C_6$-$C_{15}$ alcohol mixture with an acid or anhydride to form an ester.

19. The process of claim 18, wherein the acid or anhydride is selected from the group consisting of benzoic acid, phthalic acid, adipic acid, trimellitic acid, cyclohexanoic acid, cyclohexanoic dibasic acid, pyromellitic acid, any of the aforementioned acids' anhydrides, and mixtures thereof.

20. The process of claim 18, wherein the ester is a phthalate ester.

21. The process of claim 20, wherein the process further comprises hydrogenating the aromatic ring of the phthalate ester.

* * * * *